(12) United States Patent
Zhou et al.

(10) Patent No.: US 10,043,086 B2
(45) Date of Patent: Aug. 7, 2018

(54) LIVENESS AUTHENTICATION METHOD AND APPARATUS

(71) Applicants: BEIJING KUANGSHI TECHNOLOGY CO., LTD., Beijing (CN); PINHOLE (BEIJING) TECHNOLOGY CO., LTD., Beijing (CN)

(72) Inventors: Shuchang Zhou, Beijing (CN); Xinyu Zhou, Beijing (CN); Yuxin Wu, Beijing (CN)

(73) Assignees: BEIJING KUANGSHI TECHNOLOGY CO., LTD., Beijing (CN); PINHOLE (BEIJING) TECHNOLOGY CO., LTD., Beijing (CN)

( * ) Notice: Subject to any disclaimer, the term of this patent is extended or adjusted under 35 U.S.C. 154(b) by 197 days.

(21) Appl. No.: 14/930,203

(22) Filed: Nov. 2, 2015

(65) Prior Publication Data

US 2016/0320234 A1    Nov. 3, 2016

(30) Foreign Application Priority Data

Apr. 29, 2015    (CN) .......................... 2015 1 0214257

(51) Int. Cl.
*G01N 21/25*    (2006.01)
*G06K 9/00*    (2006.01)
*G01N 21/65*    (2006.01)
*G01N 21/64*    (2006.01)

(52) U.S. Cl.
CPC ..... *G06K 9/00906* (2013.01); *G06K 9/00255* (2013.01); *G01N 21/25* (2013.01); *G01N 21/64* (2013.01); *G01N 21/65* (2013.01)

(58) Field of Classification Search
CPC ........ G01N 21/87; G01N 21/39; G01N 21/64; G01N 21/65; B07C 5/342; G01J 1/16; G01J 1/44; G06K 9/00
See application file for complete search history.

(56) References Cited

U.S. PATENT DOCUMENTS 9,061,899 B2 *    6/2015    Rowe ..................... A61B 5/117

* cited by examiner

*Primary Examiner* — Abdullahi Nur
(74) *Attorney, Agent, or Firm* — Hamre, Schumann, Mueller & Larson, P.C.

(57) ABSTRACT

Provided are a liveness authentication method and apparatus. The method comprises: filtering out light of a first predetermined waveband from incident light incident to a first area; detecting an intensity of the filtered light as a first light intensity; and determining that a liveness authentication is failed in the case that the first light intensity satisfies a predetermined condition. The liveness authentication is performed through determining whether the incident light is cold light. In the case that the incident light is light emitted from a liquid crystal display screen, it is determined that the incident light is the cold light, and it is determined that the liveness authentication is failed.

15 Claims, 6 Drawing Sheets

LIVENESS AUTHENTICATION METHOD AND APPARATUS

TECHNICAL FIELD

The present disclosure relates to a technical field of liveness face recognition, in particular to a liveness authentication method and apparatus.

BACKGROUND

At present, an identity authentication system based on a human face has been applied widely. With a promotion of the identity authentication system based on a human face, some methods that maliciously attack human face identity authentication have been already derived.

In the most original identity authentication system based on a human face, identity authentication is performed based on a comparison between a human face image currently photographed and a human face image pre-stored. However, when a photo of a person being counterfeited is placed before a camera in an identity authentication system based on a comparison of human face images, such identity authentication system can pass a user identity authentication. In other words, a malicious user can use the photo of the person being counterfeited to make a malicious attack (i.e., photo attack). Such identity authentication system is incapable of resisting the photo attack.

With respect to the above photo attack, the identity authentication system based on a comparison of human face images has been already improved. In an improved identity authentication system based on the human face, the above photo attack is handled effectively through checking whether there is a fine action on the human face. Further, the user can be required to perform a designated action, so as to strengthen the anti-attack capability of the identity authentication system based on the human face.

However, a malicious user may still utilize a tablet computer, a smart terminal and the like to play a video or a flash to imitate the human face action of the person being counterfeited, and makes a malicious attack (i.e., flash attack) on such a basis. A video or a flash that counterfeits the human face actions of the person being counterfeited may be synthesized from images of the person being counterfeited which are obtained by means of various measures by the attacker, or may be real videos of the person being counterfeited. As a result, such video or flash is greatly deceptive. Sometimes, it is difficult for the identity authentication system based on the human face to deal with such flash attack.

Therefore, there is a need for a method and apparatus for performing liveness authentication in human face recognition.

TECHNICAL FIELD

In view of the above problem, the present disclosure is proposed to provide a liveness authentication method and apparatus, which performs liveness authentication by determining whether incident light is cold light. In the case that the incident light is light emitted from a liquid crystal display screen, the incident light mainly contains a visible light waveband, and such incident light is cold light. In this case, the liveness authentication is failed. In the case that the incident light is light produced by a human face reflecting natural light, the incident light contains not only the visible light waveband but also an invisible light waveband, such as an infrared light waveband, an ultraviolet waveband, etc. Such incident light is warm light. In this case, the liveness authentication can be passed.

According to one aspect of the present disclosure, there is provided a liveness authentication method, comprising: filtering out light of a first predetermined waveband from incident light incident to a first area; detecting an intensity of the filtered light as a first light intensity; and determining that a liveness authentication is failed in the case that the first light intensity satisfies a predetermined condition.

According to an embodiment of the present disclosure, the liveness authentication method further comprises: detecting an intensity of incident light incident to a second area as a second light intensity, the first area and the second area being not overlapped with each other, wherein said determining that a liveness authentication is failed in the case that the first light intensity satisfies a predetermined condition comprises: determining that the liveness authentication is failed in the case that the first light intensity and the second light intensity satisfy a predetermined relationship.

According to another aspect of the present disclosure, there is provided a liveness authentication apparatus, comprising: a filtering device configured to filter light of a first predetermined waveband in incident light incident to a first area; an optical-electrical converting device configured to convert the filtered light from the filtering device into a first electrical signal; and a processor configured to determine an intensity of the filtered light as a first light intensity according to the first electrical signal and determine that a liveness authentication is failed when it is determined that the first light intensity satisfies a predetermined condition.

According to an embodiment of the present disclosure, the optical-electrical converting device is further configured to convert incident light incident to a second area into a second electrical signal, the first area and the second area being not overlapped with each other, wherein the processor is configured to determine an intensity of the incident light incident to the second area as a second light intensity according to the second electrical signal, wherein said determining that a liveness authentication is failed in the case that the first light intensity satisfies a predetermined condition comprises: determining that the liveness authentication is failed in the case that the first light intensity and the second light intensity satisfy a predetermined relationship.

According to another aspect, there is provided a liveness authentication apparatus, comprising: a filtering device configured to filter light of a first predetermined waveband in incident light incident to a first area; an optical-electrical converting device configured to convert the filtered light from the filtering device into a first electrical signal; a processor; a storage; and computer program instructions stored in the storage, as executed by the processor, the computer program instructions performing the following steps: determining an intensity of the filtered light as a first light intensity according to the first electrical signal, and determining that a liveness authentication is failed in the case that it is determined the first light intensity satisfies a predetermined condition.

According to an embodiment of the present disclosure, the optical-electrical converting device is further configured to convert incident light incident to a second area into a second electrical signal, the first area and the second area being not overlapped with each other, wherein, as executed by the processor, the computer program instructions further performs the following steps: determining an intensity of the incident light incident to the second area as a second light intensity according to the second electrical signal, wherein said determining that a liveness authentication is failed in the case that the first light intensity satisfies a predetermined condition comprises: determining that the liveness authentication is failed in the case that the first light intensity and the second light intensity satisfy a predetermined relationship.

According to an embodiment of the present disclosure, the liveness authentication apparatus further comprises: at least one lens configured to enable the optical-electrical converting device to capture a scene image within a predetermined photographing range.

According to another aspect of the present disclosure, there is provided a computer program product for performing liveness authentication, comprising a computer readable storage medium on which computer program instructions are stored, wherein, as executed by a processor, the computer program instructions make the processor: determine an intensity of filtered light obtained after light of a first predetermined waveband is filtered in incident light incident to a first area as a first light intensity according to a first electrical signal produced based on the filtered light, and determine that a liveness authentication is failed in the case that it is determined the first light intensity satisfies a predetermined condition.

According to an embodiment of the present disclosure, the computer program instructions further make the processor: determine an intensity of incident light incident to a second area as a second light intensity according to a second electrical signal produced based on the incident light incident to the second area, wherein said determining that a liveness authentication is failed in the case that the first light intensity satisfies a predetermined condition comprises: determining that the liveness authentication is failed in the case that the first light intensity and the second light intensity satisfy a predetermined relationship.

The liveness authentication method and apparatus according to the embodiments of the present disclosure determine that the liveness authentication is failed in the case that it is determined the incident light is the cold light. In this case, even if the human face photo used for an attack is completely the same as the human face image pre-stored or the human face flash used for an attack is completely the same as the human face action required, this attack can be detected effectively only if the human face photo or the human flash used for the attack is played by using a liquid crystal display screen, so as to raise anti-attack capability of the identity recognition system based on the human face.

BRIEF DESCRIPTION OF THE DRAWINGS

Embodiments of the present disclosure would be described in detail by combining with the accompanying drawings, and the above and other purposes, characteristics and advantages of the present disclosure would become more evident. The figures are used to provide further understanding of the embodiments of the present disclosure, form a part of the specification, and are used to explain the present disclosure together with the embodiments of the present disclosure, but do not form a limitation to the present disclosure. In the drawings, the same reference marks generally represent the same means or steps.

DETAILED DESCRIPTION

In order to make purposes, technical solutions and advantages of the present disclosure more evident, exemplary embodiments according to the present disclosure would be described in detail by referring to the accompanying drawings. Obviously, the embodiments described below are just a part of embodiments of the present disclosure rather than all the embodiments of the present disclosure. It shall be understood that the present disclosure is not limited by the exemplary embodiments described below. Based on the embodiments of the present disclosure described below, all the other embodiments obtained by those skilled in the art without paying any inventive labor shall be deemed as falling into the protection scope of the present disclosure.

Figure 1:
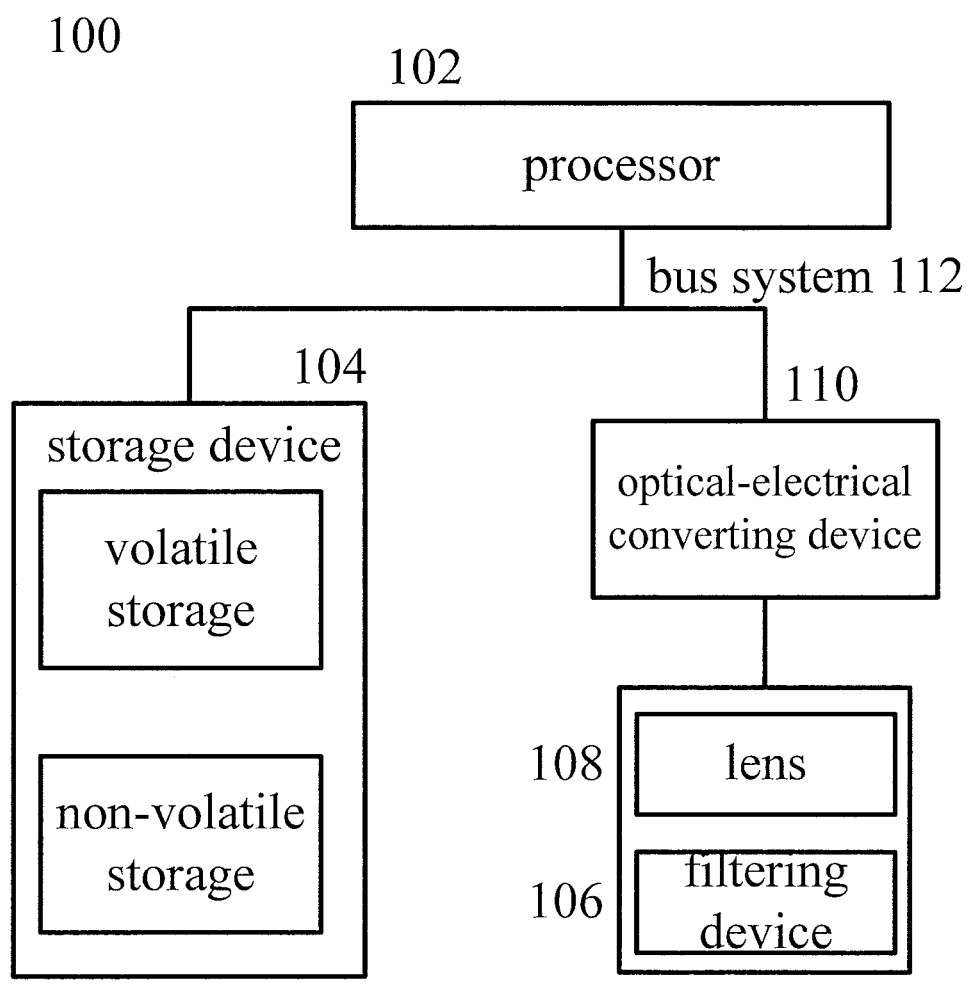
FIG. 1 is a schematic block diagram of a liveness authentication apparatus that applies a liveness authentication method according to an embodiment of the present disclosure.

First, a block diagram which can be used to implement an exemplary liveness authentication apparatus of an embodiment of the present disclosure would be described by referring to FIG. 1.

As shown in FIG. 1, a liveness authentication apparatus 100 comprises one or more processors 102, a storage device 104, one or more filtering devices 106, and one or more optical-electrical converting devices 110. These components are connected to each other through a bus system 112 and/or other forms of connecting mechanism (not shown in the figure). It shall be noted that components and structure of the liveness authentication apparatus 100 as shown in FIG. 1 are just for illustration, but not for limitation. The liveness authentication 100 may also have other components and structures according to requirements.

In addition, as shown in FIG. 1, the liveness authentication apparatus 100 can further comprise one or more lenses 108.

The processor 102 can be a central processing unit (CPU) or other forms of processing units having capabilities of data processing and/or instruction execution.

The storage device 104 can comprise one or more computer program products. The computer program product can comprise various forms of computer readable storage medium, for example, a volatile storage and/or a non-volatile storage. The volatile storage can for example comprise a random access memory (RAM) and/or a cache memory and the like. The non-volatile storage can for example comprise a read-only memory (ROM), hard disk, and a flash memory and the like. One or more computer program instructions can be stored on the computer readable storage medium. The processor 102 can execute the program instructions, so as to realize functions (realized by the processor) in the embodiments of the present disclosure described below or other desirable functions. Various application programs and various data can be stored in the computer readable storage medium, for example, human face data, various data used and/or produced by the application programs and so on.

Operations of the processor 102, the filtering device 106, the lens 108, and the optical-electrical converting device 110 in the liveness authentication apparatus 100 according to the embodiment of the present disclosure would be described in detail below.

Figure 2:
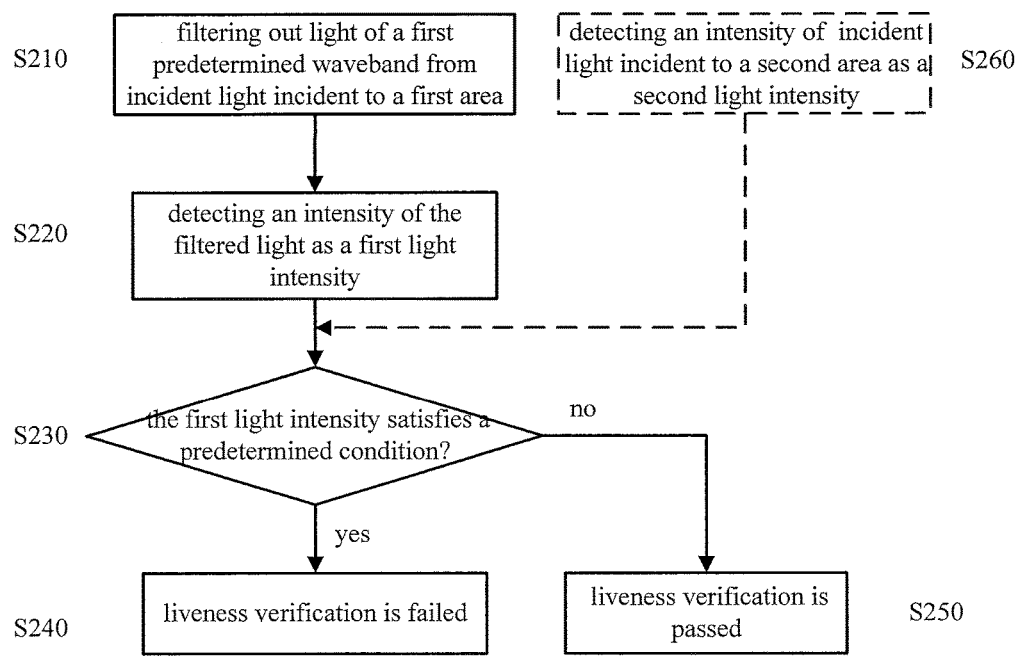
FIG. 2 is schematic flowchart of a liveness authentication method according to an embodiment of the present disclosure.

FIG. 2 is a schematic flowchart of a liveness authentication method 200 according to an embodiment of the present disclosure.

In step S210, light of a first predetermined waveband is filtered out from incident light incident to a first area. A filtering device can be utilized to filter out the light of the first predetermined waveband from the incident light incident to the filtering device. The filtering device is corresponding to the first area. The first area can be a single area or can comprise at least two sub-areas which are not overlapped with each other. For example, the first predetermined waveband can comprise a visible light waveband.

As an example, the light of the first predetermined waveband can be filtered out from the incident light incident to the first area through at least two filters. Along the light transmission direction, the at least two filters are not overlapped with each other, and the at least two sub-areas are corresponding to the at least two filters one to one.

In step S220, an intensity of the filtered light is detected as a first light intensity.

In the case that the first area is a single area, an intensity of the filtered light of this single area can be detected as the first light intensity.

According to another aspect, in the case that the first area comprises at least two sub-areas, an intensity of the filtered light from each of the at least two filters can be detected (a filter corresponding to a sub-area), and the first light intensity can be determined according to the detected intensity of the filtered light from respective filters of the at least two filters. In this case, the first light intensity can be a single light intensity, for example, an average value, a maximum value or a minimum value of the intensity of the filtered light from the respective filters of the at least two filters can be determined as the first light intensity.

Herein, it shall be understood that for each filter (each sub-area), said detecting the intensity of the filtered light from the filter can be detecting an average intensity of the filtered light from the filter or an average intensity of the filtered light from the filter with noise removed.

In step S230, it is determined whether the first light intensity satisfies a predetermined condition.

In the case that it is determined in step S230 that the first light intensity satisfies the predetermined condition, it is determined in step S240 that the liveness authentication is failed. Otherwise, in the case that it is determined in step S230 that the first light intensity does not satisfy the predetermined condition, it is determined in step S250 that the liveness authentication is passed.

As an example, in step S230, it can be determined whether the first light intensity is lower than a predetermined light intensity threshold, and in the case that it is determined that the first light intensity is lower than the predetermined light intensity threshold, it is determined that the first light intensity satisfies the predetermined condition. In the case that the visible light waveband is filtered out in step S210, it is actually determined in step S230 whether an intensity of light wavebands other than the visible light waveband in the incident light is lower than the predetermined light intensity threshold.

In addition, as shown in FIG. 2, the liveness authentication method 200 according to the embodiment of the present disclosure can further detect an intensity of incident light incident to a second area as a second light intensity in step S260, and the first area and the second area are not overlapped with each other. It shall be known that steps S210, S220 and S260 can be executed in parallel.

In this case, in step S230, it can be determined whether the first light intensity and the second light intensity satisfy a predetermined relationship, and in the case that it is determined in step S230 that the first light intensity and the second light intensity satisfy the predetermined relationship, it is determined in step S240 that the liveness authentication is failed; otherwise, in the case that it is determined in step S230 that the first light intensity and the second light intensity do not satisfy the predetermined relationship, it is determined in step S240 that the liveness authentication is passed.

As an example, in step S230, a proportion of the first light intensity and the second light intensity can be calculated as a first proportion, and in the case that the first proportion is smaller than a first predetermined threshold, it is determined that the first light intensity and the second light intensity satisfy the predetermined relationship, and thus it is determined in step S240 that the liveness authentication is failed. The first predetermined threshold is smaller than 1, and for example, the value of the first predetermined threshold may be within a range of 0.5-0.8.

Alternatively, in step S230, a difference between the second light intensity and the first light intensity can be calculated, and a proportion of the difference and the second light intensity is calculated as a second proportion. And in the case that the second proportion is greater than a second predetermined threshold, it is determined that the first light intensity and the second light intensity satisfy the predetermined relationship, and thus it is determined in step S240 that the liveness authentication is failed. The second predetermined threshold is smaller than 1, and for example the value of the second predetermined threshold can be within a range of 0.2-0.5.

As another example, in step S230, a maximum value and a minimum value of the first light intensity and the second light intensity can be determined. In the case that a proportion of the minimum value and the maximum value is smaller than the first predetermined threshold, it is determined that the first light intensity and the second light intensity satisfy the predetermined relationship, and thus it is determined in step S240 that the liveness authentication is failed.

Alternatively, in step S230, the maximum value and the minimum value of the first light intensity and the second light intensity can be determined, and the difference between the maximum value and the minimum value can be calculated. And in the case that the proportion of the difference and the maximum value is greater than the second predetermined threshold, it is determined that the first light intensity and the second light intensity satisfy the predetermined relationship, and thus it is determined in step S240 that the liveness authentication is failed.

According to another aspect, in the case that the first area comprises at least two sub-areas, the intensity of the filtered light from each of the at least two filters can be detected in step S220, and the detected intensity of the filtered light from respective filters of the at least two filters can be jointly taken as the first light intensity. In this case, the first light intensity can comprise at least two light intensity components, which are corresponding to the at least two filters one to one.

In this case, when the maximum value and the minimum value of the first light intensity and the second light intensity are determined in step S230, it can be determined that the maximum value and the minimum value of the second light intensity and the at least two light intensity components of the first light intensity can be determined.

For example, there are n light intensity detection areas comprising the second area and respective filtering sub-areas of the first area, wherein the intensity of the filtered light is detected in respective filtering sub-areas of the first area, and the intensity of the incident light incident to the second area is detected in the second area, $x_i$ is the intensity of the light corresponding to the $i^{th}$ light intensity detection area, $\alpha$ is the first predetermined threshold, and $\beta$ is the second predetermined threshold. In step S230, it can be determined whether the first light intensity and the second light intensity satisfy he predetermined condition according to following equation (1) or (2).

$$\frac{\max(x_1, \ldots, x_n) - \min(x_1, \ldots x_n)}{\max(x_1, \ldots, x_n)} > \alpha \quad (1)$$

$$\frac{\min(x_1, \ldots x_n)}{\max(x_1, \ldots, x_n)} < \beta \quad (2)$$

According to the embodiment of the present disclosure, when a display image, a video or a flash on the liquid crystal display screen is utilized to make an attack, the incident light incident to the first area and the second area contains a large amount of visible light components, and the obtained first light intensity and second light intensity have evident distinction. In this case, an attack of the screen display can be certainly detected, that is, the liveness authentication is failed.

However, according to the embodiment of the present disclosure, even if the liveness authentication is passed, it does not mean that there must be a liveness. For example, in the case that there is no liveness and there is no display of the liquid crystal display screen, "no" may be obtained in step S230, and it is also determined in step S250 that the liveness authentication is passed. Therefore, the liveness authentication method according to the embodiment of the present disclosure is just one aspect of performing the liveness authentication in the human face recognition system, and aims at resisting the attack from the image display, video display or flash display of the liquid crystal display screen.

In order to ensure a normal operation of the liveness authentication method according to the embodiment of the present disclosure, it is necessary to ensure that the ambient light contains a large amount of invisible light components, for example, infrared light component and/or ultraviolet light component, i.e., ensuring that the ambient light is the warm light. If the ambient light per se is the cold light, i.e., not containing invisible light components or only containing very few invisible light components, then the false alarm probability of the liveness authentication method according to the embodiment of the present disclosure would be extremely high.

The liveness authentication method according to the embodiment of the present disclosure can be used independently, or can be used simultaneously with other liveness authentication methods.

Below, a liveness authentication apparatus according to the embodiments of the present disclosure would be described by referring to FIGS. 3-8.

Figure 3:
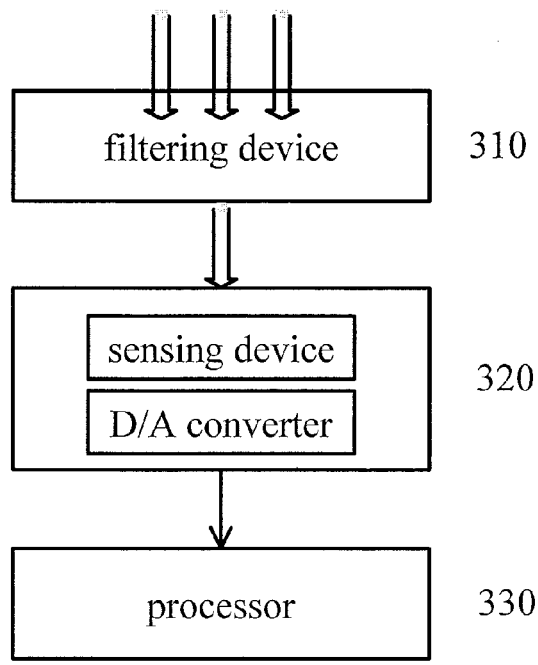
FIG. 3 is a schematic block diagram of a liveness authentication apparatus according to an embodiment of the present disclosure.

FIG. 3 is a schematic block diagram of a liveness authentication apparatus 300 according to an embodiment of the present disclosure.

As shown in FIG. 3, the liveness authentication apparatus 300 according to the embodiment of the present disclosure comprises: a filtering device 310, an optical-electrical converting device 320, and a processor 330.

The filtering device 310 is configured to filter out light of a first predetermined waveband from incident light incident to a first area. The filtering device 310 is corresponding to the first area which can be a single area or can comprise at least two sub-areas which are not overlapped with each other. The filtering device 310 can comprise at least two filters. Along the light transmission direction, the at least two filters are not overlapped with each other, and the at least two sub-areas are corresponding to the at least two filters one to one.

The optical-electrical converting device 320 is configured to convert the filtered light from the filtering device 310 into a first electrical signal. The optical-electrical converting device 320 can comprise a sensing device and an analog-to-digital (D/A) converter. The sensing device is configured to convert the filtered light from the filtering device 310 into an analog electrical signal, and the analog-to-digital converter is configured to convert the analog electrical signal into a digital electrical signal, the first electrical signal being the digital electrical signal.

The processor 330 is configured to determine an intensity of the filtered light as a first light intensity according to the first electrical signal and determine that the liveness authentication is failed in the case that it is determined that the first light intensity satisfies a predetermined condition.

On one hand, in the case that the first area is a single area, the optical-electrical converting device 320 can convert the filtered light from the single area (the filtering device 310) into the first electrical signal. The processor 330 determines the first light intensity according to the first electrical signal.

On the other hand, in the case that the first area comprises at least two sub areas, the optical-electrical converting device 320 can convert the filtered light from respective filters of the at least two filters of the filtering device 310 into electrical signals. Such electrical signals can be generally referred to as the first electrical signal. The processor 330 determines the intensity of the filtered light from respective filters of the at least two filters of the filtering device 310 according to the first electrical signal, and determines the first light intensity according to the determined intensity of the filtered light from respective filters of the filtering device 310. In this case, the first light intensity can be a single light intensity, for example, the processor 330 can determine an average value, a maximum value or a minimum value of the intensity of the filtered light from respective filters of the at least two filters of the filtering device 310 as the first light intensity.

In addition, the processor 330 can determine whether the first light intensity is lower than the predetermined light intensity threshold. And in the case that it is determined the first light intensity is lower than the predetermined light intensity threshold, it is determined that the first light intensity satisfies the predetermined condition, and thus it is determined that the liveness authentication is failed.

As an example, the first predetermined waveband can comprise a visible light waveband. In this case, the filtering device 310 can filter out the visible light waveband from the incident light incident to the first area. The optical-electrical converting device 320 converts the light in which the visible light waveband has been filtered out into the first electrical signal. In other words, in the case that the filtering device 310 has filtered out the visible light waveband, the processor 330 actually determines whether an intensity of light of wavebands other than the visible light waveband in the incident light incident to the first area is lower than the predetermined light intensity threshold, and in the case that the intensity of light of the wavebands other than the visible light waveband in the incident light incident to the first area is lower than the predetermined light intensity threshold, it is determined that the liveness authentication is failed.

In addition, the optical-electrical converting device 320 can be further configured to convert the incident light incident to the second area into the second electrical signal. The first area and the second area are not overlapped with each other.

In this case, the processor 330 further determines the intensity of the incident light incident to the second area as the second light intensity according to the second electrical signal, and in the case that it is determined the first light intensity and the second light intensity satisfy the predetermined relationship, it is determined that the liveness authentication is failed.

As an example, the processor 330 can calculate a proportion of the first light intensity and the second light intensity as a first proportion, and in the case that the first proportion is smaller than a first predetermined threshold, it is determined that the first light intensity and the second light intensity satisfy the predetermined relationship, and thus it is determined that the liveness authentication is failed. The first predetermined threshold is smaller than 1, and for example, the value of the first predetermined threshold may be within a range of 0.5-0.8.

Alternatively, the processor 330 can calculate a difference between the second light intensity and the first light intensity, and calculate a proportion of the difference and the second light intensity as a second proportion. In the case that the second proportion is greater than a second predetermined threshold, it is determined that the first light intensity and the second light intensity satisfy the predetermined relationship, and thus it is determined that the liveness authentication is failed. The second predetermined threshold is smaller than 1, and for example, the value of the second predetermined threshold can be within a range of 0.2-0.5.

As another example, the processor 330 can determine a maximum value and a minimum value of the first light intensity and the second light intensity. In the case that a proportion of the minimum value and the maximum value is smaller than the first predetermined threshold, it is determined that the first light intensity and the second light intensity satisfy the predetermined relationship, and thus it is determined that the liveness authentication is failed.

Alternatively, the processor 330 can determine the maximum value and the minimum value of the first light intensity and the second light intensity, and calculate the difference between the maximum value and the minimum value. And in the case that the proportion of the difference and the maximum value is greater than the second predetermined threshold, it is determined that the first light intensity and the second light intensity satisfy the predetermined relationship, and thus it is determined that the liveness authentication is failed.

In the case that the first area comprises at least two sub-areas, when the processor 330 determines the intensity of the filtered light from respective filters of the at least two filters of the filtering device 310, the processor 330 can jointly take intensity of the filtered light from respective filters of the filtering device 310 as the first light intensity. In this case, the first light intensity can comprise at least two light intensity components which are corresponding to the at least two filters one to one.

In this case, the processor 330 can determine the maximum value and the minimum value of the second light intensity and the at least two light intensity components of the first light intensity, so as to be taken as the maximum value and the minimum value of the first light intensity and the second light intensity.

According to the embodiment of the present disclosure, when a display image, a video or a flash on a liquid crystal display screen is utilized to make an attack, the incident light incident to the first area and the second area contains a large amount of visible light components, and the obtained first light intensity and second light intensity have evident distinction. In this case, an attack of the screen display can be certainly detected, that is, the liveness authentication is failed.

Figure 4:
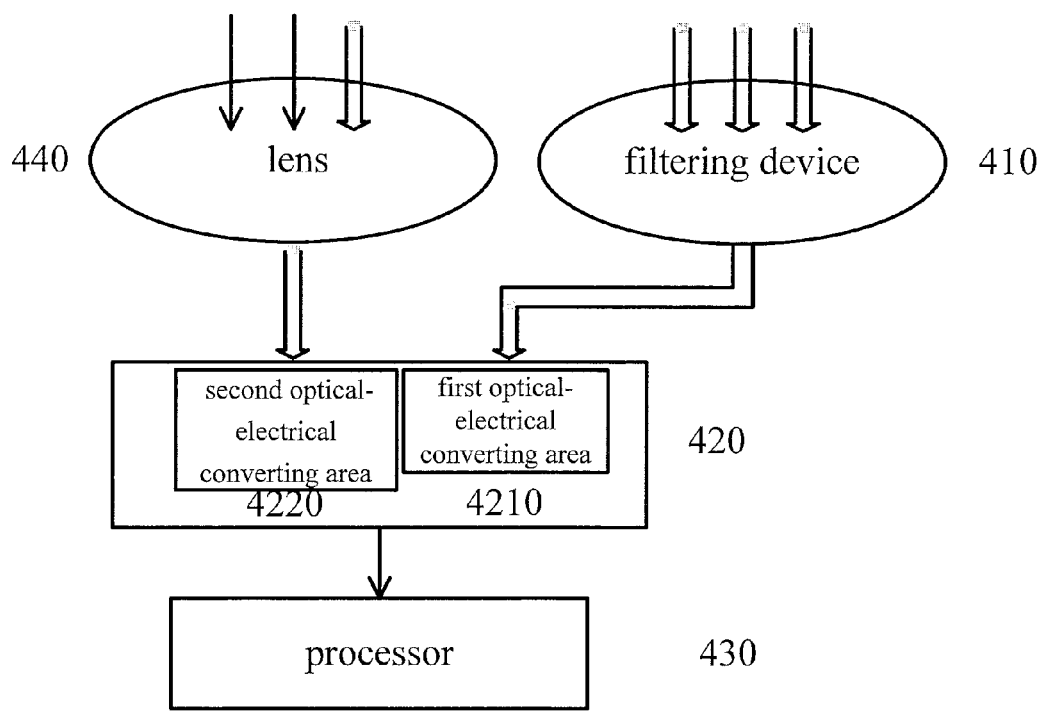
FIG. 4 is a schematic block diagram of a specific implementation of a liveness authentication apparatus according to an embodiment of the present disclosure.

FIG. 4 is a schematic block diagram of a specific implementation of a liveness authentication apparatus according to an embodiment of the present disclosure.

As shown in FIG. 4, the liveness authentication apparatus 400 according to the embodiment of the present disclosure comprises a filtering device 400, at least one lens 440, an optical-electrical converting device 420, and a processor 430.

The at least one lens 440 is configured to enable the optical-electrical converting device 420 to capture a scene image within a predetermined photographing range.

Along the light transmission path, the filtering device 410 and the at least one lens 440 are not overlapped with each other, and the at least one lens 440 is not overlapped with each other. In this embodiment, the filtering device 410 provides the first area, and the at least one lens 440 provides the second area. The filtering device 410 can be the same as the filtering device 310 described in FIG. 3, and thus details are not further given herein.

The optical-electrical converting device 420 comprises a first optical-electrical converting area 4210 and a second optical-electrical converting area 4220. The first optical-electrical converting area 4210 is corresponding to the filtering device 410, and the second optical-electrical converting area 4220 is corresponding to the at least one lens 440.

The filtering device 410 filters out light of a first predetermined waveband from incident light incident to a first area, and the first optical-electrical converting area 4210 produces a first electrical signal based on the filtered light from the filtering device 410. The second optical-electrical converting area 4220 produces a second electrical signal based on the light penetrating the lens 440.

The processor 430 determines an intensity of the filtered light from the filtering device 410 as a first light intensity according to the first electrical signal, and determines an intensity of the light penetrating the lens 440 as a second light intensity according to the second electrical signal. And in the case that it is determined that the first light intensity and the second light intensity satisfy the predetermined relationship, it is determined that the liveness authentication is failed.

The operation of the processor 430 can be the same as the operation of the processor 330 as described by referring to FIG. 3, and thus details are not further given herein.

Figure 5A:
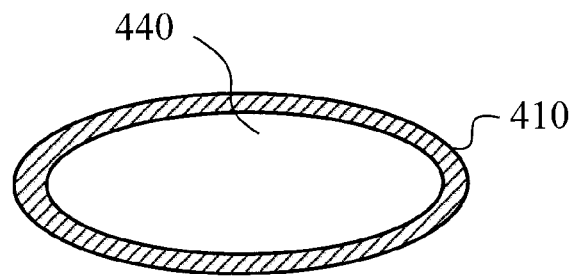
FIGS. 5A-5B are two exemplary layout diagrams of a filtering device according to an embodiment of the present disclosure.
Figure 5B:
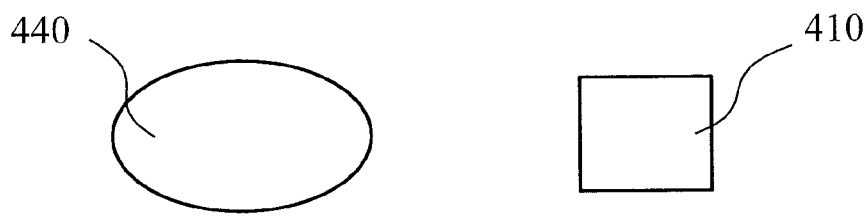

As shown in FIG. 5A, the filtering device 410 can be embedded in the periphery of a part of the at least one lens 440. In this case, the filtering device 410 can be arranged for example as a ring shape or a shape with its inner edge being a circular shape and outer edge being a rectangle. As shown in FIG. 5B, the filtering device 410 can be arranged separately from the at least one lens 440.

Figure 6:
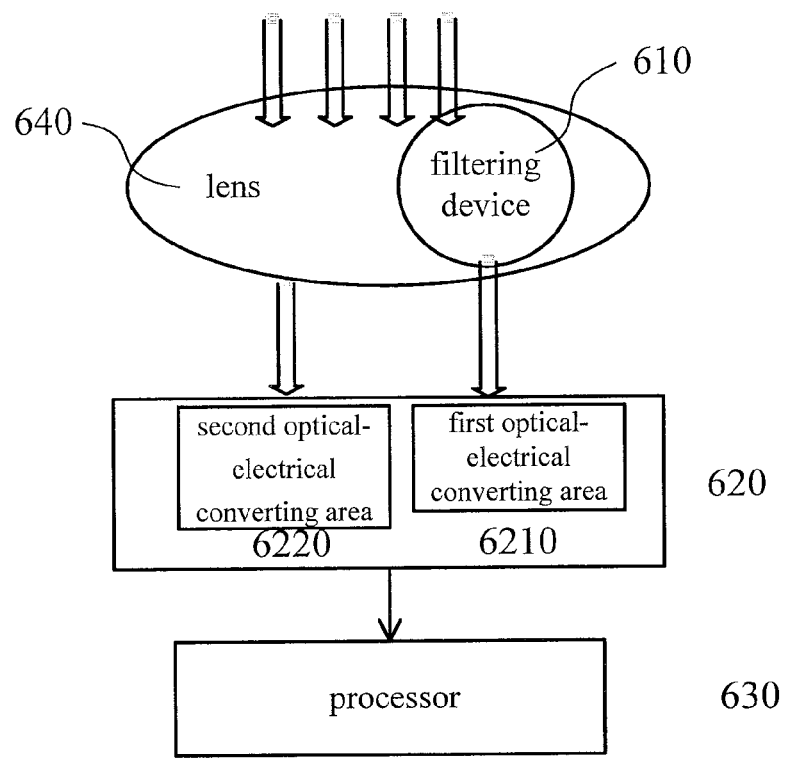
FIG. 6 is a schematic block diagram of another specific implementation of a liveness authentication apparatus according to an embodiment of the present disclosure.

FIG. 6 is a schematic block diagram of another specific implementation of a liveness apparatus according to an embodiment of the present disclosure.

As shown in FIG. 6, the liveness authentication apparatus 600 according to the embodiment of the present disclosure comprises a filtering device 610, at least one lens 640, an optical-electrical converting device 620, and a processor 630.

The at least one lens 640 is configured to enable the optical-electrical converting device 620 to capture a scene image within a predetermined photographing range.

Along the light transmission path, the filtering device 610 is overlapped with a part of the at least one lens 640. In particular, the filtering device 610 can be integrated with the part of the at least one lens 640, or can be attached to the part of the at least one lens 640. For example, the filtering device 610 is arranged in front of the at least one lens 640, which is arranged in front of the optical-electrical converting device 620 and has a predetermined distance from the optical-electrical converting device 620. Alternatively, the filtering device 610 is arranged behind the at least one lens 640, which is arranged in front of the optical-electrical converting device 620 and has a predetermined distance from the optical electrical converting device 620.

As an example, the at least one lens 640 is one lens. In this case, the filtering device is overlapped with a part of the lens.

As another example, the at least one lens 640 comprises a plurality of lenses. In this case, the filtering device is overlapped with at least one portion of a part of the plurality of lenses, and overlapped or not overlapped with one portion of other lens. In particular, for example, the at least one lens 640 comprises two lenses. The filtering device can be overlapped with one portion of each of the two lenses, or can be overlapped with one portion of a first lens of the two lenses but not overlapped with a second lens, or can be overlapped with the whole first lens but not overlapped with the second lens, or can be overlapped with the whole first lens but overlapped with one portion of the second lens.

The portion of the at least one lens 640 overlapped with the filtering device 610 provides the first area, while the portion of the at least one lens 640 not overlapped with the filtering device 640 provides the second area.

Figure 7A:
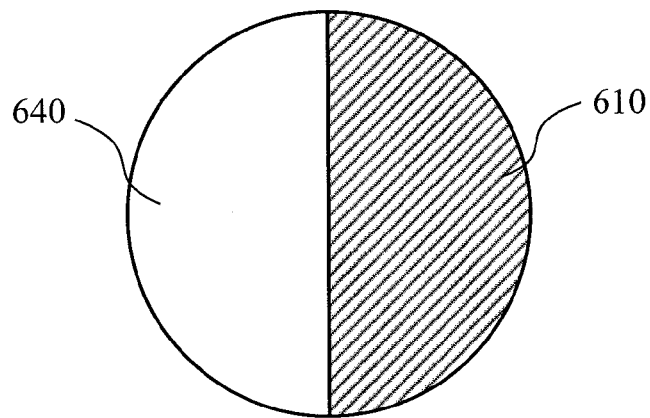
FIGS. 7A-7C are three exemplary layout diagrams of a filtering device on one lens according to an embodiment of the present disclosure.
Figure 7B:
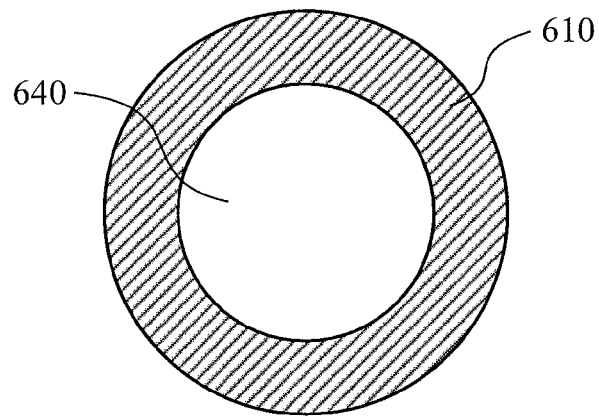
Figure 7C:
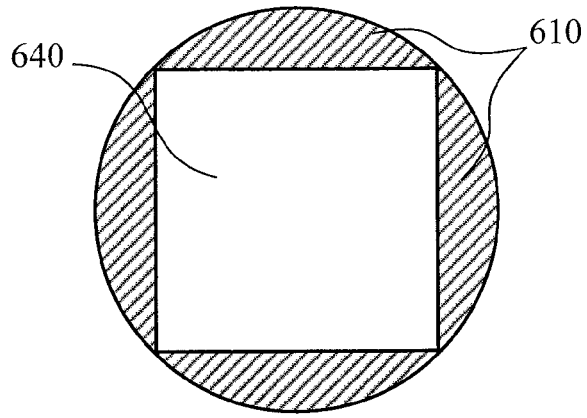

FIGS. 7A-7C show several exemplary arrangements of the filtering device 610 on one lens 640. As shown in FIG. 7A, the filtering device 610 comprises one filtering sub-area (first area), which can be overlapped with the right half portion of the lens 640; as shown in FIG. 7B, the filtering device 610 comprises a ring-shape filtering sub-area (first area), which is coincided with the ring shape of the lens 640 that starts from the outer edge; as shown in FIG. 7C, the filtering device 610 comprises four separate filtering sub-areas.

The filtering device 610 can be similar to the filtering device 310 as described by referring to FIG. 3, and their distinction only lies in that the filtering device 310 comprises one or more filters, while the filtering device 610 (the first area) comprises one or more filtering sub-areas distributed on the lens 640 and not overlapped with each other.

As shown in FIG. 6, the optical-electrical converting device 620 can comprise a first optical-electrical converting area 6210 and a second optical-electrical converting area 6220.

The first area is corresponding to the first optical-electrical converting area 6210, which produces the first electrical signal based on the filtered light from the filtering device 610.

The second area is corresponding to the second optical-electrical converting area 6220, which produces the second electrical signal based on the incident light incident to the second area.

The first optical-electrical converting area 6210 can produce the first electrical signal according to the way described by referring to FIG. 3, and the second optical-electrical converting area 6220 can produce the second electrical signal according to the way described by referring to FIG. 3.

In the case that the first area comprises at least two filtering sub-areas, for each of the at least filtering sub-areas, the processor 630 determines the intensity of the filtered light from the filtering sub-area according to the electrical signal produced by the first optical-electrical converting area 6210 and corresponding to the filtering sub-area. Then, the processor 630 determines an average value, a minimum value or a maximum value of the intensity of the filtered light from respective filtering sub-areas of the at least two filtering sub-areas as the first light intensity. Alternatively, the processor 630 jointly takes the intensity of the filtered light from respective filtering sub-areas of the at least two filtering sub-areas as the first light intensity.

For example, the processor 630 can determine the intensity of the filtered light from the first area containing one filtering sub-area as shown in FIGS. 7A and 7B as the first light intensity, and can determine an average value, a maximum value or a minimum value of the intensity of the light of respective filtering sub-areas in the first area containing four filtering sub-areas as shown in FIG. 7C as the first light intensity, or can jointly take the intensity of the light of the respective filtering sub-areas in the first area containing four filtering-sub areas as shown in FIG. 7C as the first light intensity.

Later, the operation of the processor 630 can be similar to the operation of the processor 330 as described by referring to FIG. 3, and thus no further description is given herein.

Figure 8:
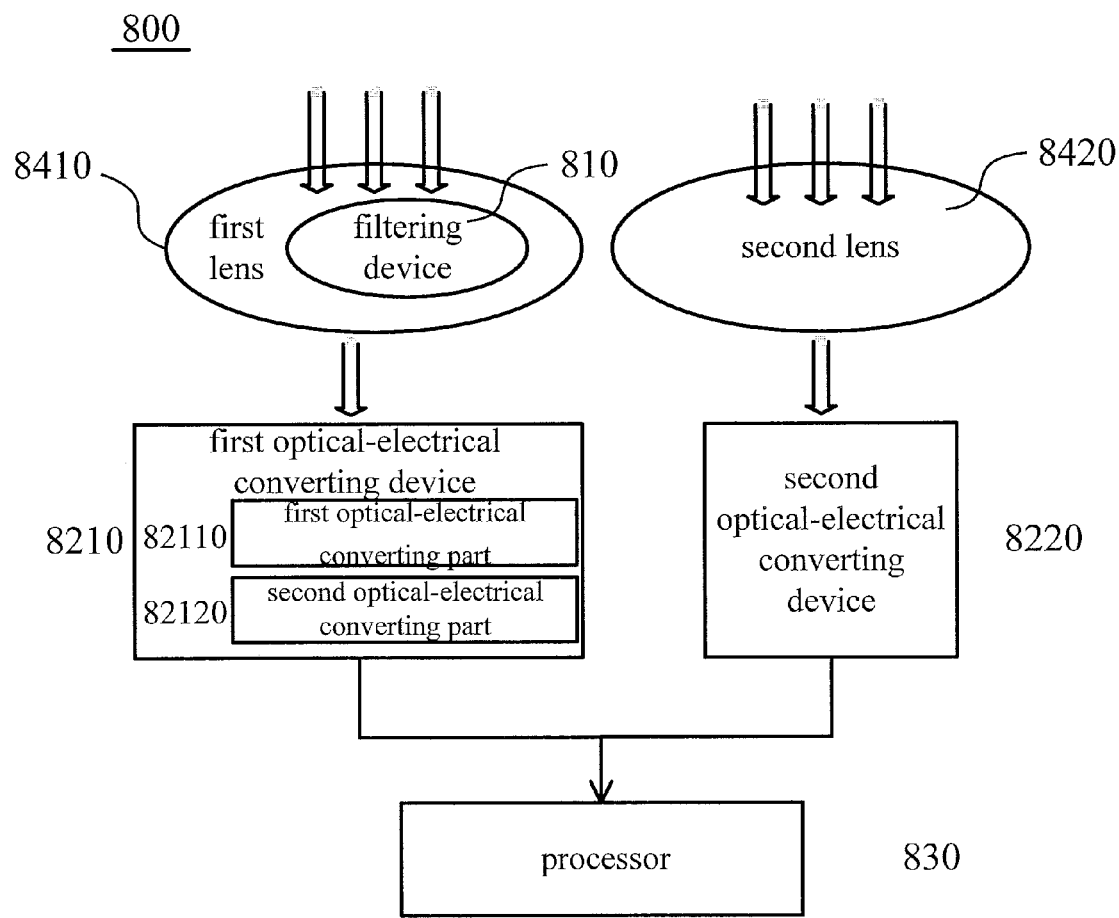
FIG. 8 is a schematic block diagram of a specific implementation of a liveness authentication apparatus according to an embodiment of the present disclosure.

FIG. 8 is a schematic block diagram of a specific implementation of a liveness authentication apparatus 800 according to an embodiment of the present disclosure.

As shown in FIG. 8, the liveness authentication apparatus 800 according to the embodiment of the present disclosure comprises a filtering device 810, a first lens 8410, a second lens 8420, a first optical-electrical converting device 8210, a second optical-electrical converting device 8220 and a processor 830.

The first lens 8410 is corresponding to the first optical-electrical converting device 8210, and the second lens 8420 is corresponding to the second optical-electrical converting device 8220.

The first lens 8410 is configured to enable the first optical-electrical converting device 8210 to capture a scene image within a first predetermined photographing range.

The second lens 8420 is configured to enable the second optical-electrical converting device 8220 to capture a scene image within a second predetermined photographing range.

The first predetermined photographing range is at least partially overlapped with the second predetermined photographing range.

The filtering device 810 is overlapped with at least one portion of the first lens 8410. Along the light transmission path, the filtering device 810 is arranged in front of or behind the first lens 8410, the filtering device 810 and the first lens 8410 are arranged in front of the first optical-electrical converting device 8210 and have a predetermined distance from the first optical-electrical converting device 820, and the second lens 8420 is arranged in front of the second optical-electrical converting device 8220 and has a predetermined distance from the second optical-electrical converting device 8220.

In the case that the filtering device 810 is overlapped with an entire area of the first lens 8410, the first optical-electrical converting device 8210 converts the light penetrating the first lens 8410 into the first electrical signal. The second optical-electrical converting device 8220 converts the light penetrating the second lens 8420 into the second electrical signal.

In the case that the filtering device 810 is overlapped with a partial area of the first lens, the first optical-electrical converting device 8210 can comprise a first optical-electrical converting part 82110 and a second optical-electrical converting part 82120.

The portion of the first lens 8410 overlapped with the filtering device 810 provides the first area; and the portion of the first lens 8410 not overlapped with the filtering device 810 and the second lens 8420 provide the second area.

The first optical-electrical converting part 82110 of the first optical-electrical converting device 8210 is corresponding to the first optical-electrical converting area 6210 as shown in FIG. 6, and the second optical-electrical converting part 82120 of the first optical-electrical converting device 8210 and the second optical-electrical converting device 8220 are corresponding to the second optical-electrical converting area 6220 as shown in FIG. 6.

The portion (the first area) of the first lens 8410 overlapped with the filtering device 810 is corresponding to the first optical-electrical converting part 82110 (the first optical-electrical converting area) of the first optical-electrical converting device 8210, and the first optical-electrical converting part 82110 (the first optical-electrical converting area) of the first optical-electrical converting device 8210 produces the first electrical signal based on the filtered light from the filtering device.

The portion (the first part of the second area) of the first lens 8410 not overlapped with the filtering device 810 is corresponding to the second optical-electrical converting part 82120 (the first part of the second optical-electrical converting area) of the first optical-electrical converting device 8210, and the second optical-electrical converting part 82120 (the first part of the second optical-electrical converting area) of the first optical-electrical converting device 8210 produces the first part of the second electrical signal based on incident light incident to the portion of the first lens 8410 not overlapped with the filtering device 810.

The second lens 8420 (the second part of the second area) is corresponding to the second optical-electrical converting device 8220 (the second part of the second optical-electrical converting area), and the second optical-electrical converting device 8220 (the second part of the second optical-electrical converting area) produces the second part of the second electrical signal based on the incident light incident to the second lens 8420.

The filtering device 810 can be similar to the filtering device 310 as described by referring FIG. 3, or can be similar to the filtering device 610 as described by referring to FIGS. 6 and 7A-7C, but is not limited thereto.

The processor 830 produces the first light intensity based on the first electrical signal, and produces the second light intensity based on at least one of the first part and second part of the second electrical signal.

In addition, the processor 830 can produce an image signal based on at least one of the first part and second part of the second electrical signal.

In addition, the processors 330, 430, 630 and 830 according to the embodiments of the present disclosure can not only be implemented as one or more general processors, but also be implemented by utilizing a single chip microcomputer, a microprocessor, a digital signal processor, a special image processing chip, and a filed programmable logic array and so on.

According to the embodiments of the present disclosure, based on the display characteristics of the liquid crystal display screen, it is identified whether the incident light is the cold light through detecting components in the incident light other than the visible light components, i.e., correspondingly identifying whether the incident light is the light emitted from the liquid crystal display screen. In the case that it is determined that the incident light is the light emitted from the liquid crystal display screen, it can be determined that an attack of screen display is detected, that is, the liveness authentication is failed.

According to the embodiments of the present disclosure, even if the liveness authentication is passed, it does not mean that there is a liveness. The liveness authentication method and apparatus according to the embodiments of the present disclosure are just one aspect of performing the liveness authentication in the human face recognition system, and aims at resisting the attack from the image display, video display or flash display of the liquid crystal display screen.

In order to ensure a normal operation of the liveness authentication method and apparatus according to the embodiment of the present disclosure, it is necessary to ensure that the ambient light contains a large amount of invisible light components, for example, infrared light component and/or ultraviolet light component, i.e., ensuring that the ambient light is the warm light. If the ambient light per se is the cold light, i.e., not containing invisible light components or only containing very few invisible light components, then the false alarm probability of the liveness authentication method according to the embodiment of the present disclosure would be extremely high.

Although exemplary embodiments are already described herein by referring to the accompanying drawings, it shall be understood that the above exemplary embodiments are just for illustration, and do not intend to limit the scope of the present disclosure thereto. Those ordinary skilled in the art can make various alternations and amendments without departing from the scope and spirit of the present disclosure. All these alternations and amendments intend to be included in the scope of the present disclosure claimed in the Claims.

What is claimed is:
1. A liveness authentication method, comprising:
 filtering out light of a first predetermined waveband from incident light incident to a first area;
 detecting an intensity of the filtered light as a first light intensity;

determining that a liveness authentication is failed in the case that the first light intensity satisfies a predetermined condition; and detecting an intensity of incident light incident to a second area as a second light intensity, the first area and the second area being not overlapped with each other, wherein said determining that a liveness authentication is failed in the case that the first light intensity satisfies a predetermined condition comprises:

determining that the liveness authentication is failed in the case that the first light intensity and the second light intensity satisfy a predetermined relationship.

2. The liveness authentication method according to claim 1, wherein the first area comprises at least two sub-areas which are not overlapped with each other;

wherein said filtering out light of a first predetermined waveband from incident light incident to a first area comprises:

filtering out the light of the first predetermined waveband from the incident light incident to the first area through at least two filters, wherein the at least two filters are not overlapped with each other, and the at least two sub areas are corresponding to the at least two filters one to one.

3. The liveness authentication method according to claim 2, wherein said detecting an intensity of the filtered light as a first light intensity comprises:

detecting an intensity of the filtered light from each of the at least two filters, and determining an average value, a maximum value or a minimum value of the intensity of the filtered light from respective filters of the at least two filters as the first light intensity, or jointing taking the intensity of the filtered light from respective filters of the at least two filters as the first light intensity.

4. The liveness authentication method according to claim 1, wherein the first light intensity is a single light intensity, and said determining that the liveness authentication is failed in the case that the first light intensity and the second light intensity satisfy the predetermined relationship comprises:

calculating a proportion of the first light intensity and the second light intensity as a first proportion, and determining that the liveness authentication is failed in the case that the first proportion is smaller than a first predetermined threshold; or calculating a difference between the second light intensity and the first light intensity, calculating a proportion of the difference and the second light intensity as a second proportion, and determining that the liveness authentication is failed in the case that the second proportion is greater than a second predetermined threshold.

5. The liveness authentication method according to claim 1, wherein said determining that the liveness authentication is failed in the case that the first light intensity and the second light intensity satisfy a predetermined relationship comprises:

determining a maximum value and a minimum value of the first light intensity and the second light intensity, and determining that the liveness authentication is failed in the case that a proportion of the minimum value and the maximum value is smaller than the first predetermined threshold; or determining the maximum value and the minimum value of the first light intensity and the second light intensity, calculating a difference between the maximum value and the minimum value, and determining that the liveness authentication is failed in the case that a proportion of the difference and the maximum value is greater than the second predetermined threshold.

6. The liveness authentication method according to claim 1, wherein the first predetermined waveband comprises a visible light waveband.

7. A liveness authentication apparatus, comprising:

a filtering device configured to filter out light of a first predetermined waveband from incident light incident to a first area;

an optical-electrical converting device configured to convert the filtered light from the filtering device into a first electrical signal; and a processor configured to determine an intensity of the filtered light as a first light intensity according to the first electrical signal and determine that a liveness authentication is failed in the case that it is determined the first light intensity satisfies a predetermined condition, wherein the optical-electrical converting device is further configured to convert incident light incident to a second area into a second electrical signal, the first area and the second area being not overlapped with each other, wherein the processor is configured to determine an intensity of the incident light incident to the second area as a second light intensity according to the second electrical signal, wherein said determining that a liveness authentication is failed in the case that it is determined that the first light intensity satisfies a predetermined condition comprises:

determining that the liveness authentication is failed in the case that the first light intensity and the second light intensity satisfy a predetermined relationship.

8. The liveness authentication apparatus according to claim 7, further comprising:

at least one lens configured to enable the optical-electrical converting device to capture a scene image within a predetermined photographing range.

9. The liveness authentication apparatus according to claim 8, wherein, along a light transmission path, the filtering device is not overlapped with the at least one lens;

the filtering device provides the first area; and the at least one lens provides the second area.

10. The liveness authentication apparatus according to claim 8, wherein, along a light transmission path, the filtering device is overlapped with a part of the at least one lens, and the at least one lens is arranged in front of the optical-electrical converting device and has a predetermined distance from the optical-electrical converting device;

the part of the at least one lens overlapped with the filtering device provides the first area; and the part of the at least one lens not overlapped with the filtering device provides the second area.

11. The liveness authentication apparatus according to claim 7, wherein the optical-electrical converting device comprises a first optical-electrical converting area and a second optical-electrical converting area, the first area is corresponding to the first optical-electrical converting area, and the first optical-electrical converting area produces the first electrical signal based on the filtered light from the filtering device; and the second area is corresponding to the second optical-electrical converting area, and the second optical-electrical converting area produces the second electrical signal based on the incident light incident to the second area.

12. The liveness authentication apparatus according to claim 11, wherein the first area comprises at least two filtering sub-areas which are not overlapped with each other,
for each of the at least two filtering sub-areas, the processor determines an intensity of the filtered light from the filtering sub-area according to the first electrical signal produced by the first optical-electrical converting area and corresponding to the filtering sub-area; and
the processor determines an average value, a minimum value or a maximum value of the intensity of the filtered light from the respective filtering sub-areas of the at least two filtering sub-areas as the first light intensity, or jointly takes the intensity of the filtered light from the respective filtering sub-areas of the at least two filtering sub-areas as the first light intensity.

13. The liveness authentication method according to claim 7, wherein the first light intensity is a single light intensity, and said determining that the liveness authentication is failed in the case that the first light intensity and the second light intensity satisfy the predetermined relationship comprises:
calculating a proportion of the first light intensity and the second light intensity as a first proportion, and determining that the liveness authentication is failed in the case that the first proportion is smaller than a first predetermined threshold; or
calculating a difference between the second light intensity and the first light intensity, calculating a proportion of the difference and the second light intensity as a second proportion, and determining that the liveness authentication is failed in the case that the second proportion is greater than a second predetermined threshold.

14. The liveness authentication apparatus according to claim 7, wherein said determining that the liveness authentication is failed in the case that the first light intensity and the second light intensity satisfy a predetermined relationship comprises:
the processor determines a maximum value and a minimum value of the first light intensity and the second light intensity, and determines that the liveness authentication is failed in the case that a proportion of the minimum value and the maximum value is smaller than the first predetermined threshold; or
the processor determines the maximum value and the minimum value of the first light intensity and the second light intensity, determines a difference between the maximum value and the minimum value, and determines that the liveness authentication is failed in the case that a proportion of the difference and the maximum value is greater than the second predetermined threshold.

15. The liveness authentication apparatus according to claim 7, wherein the first predetermined waveband comprises a visible light waveband.

* * * * *